United States Patent [19]
Prince

[11] Patent Number: 6,013,200
[45] Date of Patent: Jan. 11, 2000

[54] LOW TOXICITY CORROSION INHIBITOR

[75] Inventor: Philippe Prince, Pearland, Tex.

[73] Assignee: Baker Hughes Incorporated, Houston, Tex.

[21] Appl. No.: 08/961,690

[22] Filed: Oct. 31, 1997

Related U.S. Application Data

[60] Provisional application No. 60/046,382, May 13, 1997.

[51] Int. Cl.$^7$ .............................. C09K 3/00; C07D 233/30
[52] U.S. Cl. ...................... 252/391; 548/324.5; 508/272; 508/284
[58] Field of Search ........................ 252/391; 548/324.5; 508/272, 284

[56] References Cited

U.S. PATENT DOCUMENTS

| | | | |
|---|---|---|---|
| 2,613,211 | 10/1952 | Hurwitz et al. | 548/324.5 |
| 2,613,212 | 10/1952 | Hurwitz et al. | 548/313.7 |
| 2,767,184 | 10/1956 | McKay et al. | 548/324.5 |
| 2,895,961 | 7/1959 | Hughes | 252/391 |
| 2,926,169 | 1/1960 | Hughes | 260/309.6 |
| 3,232,933 | 2/1966 | Gündel | 260/247.1 |
| 3,414,521 | 12/1968 | Teumac | 252/391 |
| 4,388,213 | 6/1983 | Oppenlaender et al. | 252/391 |
| 5,399,706 | 3/1995 | Dochniak | 548/324.5 |
| 5,496,907 | 3/1996 | Dochniak | 548/324.5 |

FOREIGN PATENT DOCUMENTS

| | | |
|---|---|---|
| 0060455 | 9/1982 | European Pat. Off. . |
| 96-26189 | 8/1996 | WIPO . |

OTHER PUBLICATIONS

WPI Abstract of JP 58 207 377 A; week 3 of 1984.
WPI Abstract of JP 62 250 043 A; week 49 of 1987.
DIALOG® print–out of Derwent WPI Abstract 81–22089D/198113 of JP 56010171, 1981.
DIALOG® print–out of *Chemical Abstract* 110(16)143459g, 1989.
DIALOG® print–out of *Chemical Abstract* 103(17)141959b, 1985.
DIALOG® print–out of *Chemical Abstract* 100(22)178720f, 1983.

*Primary Examiner*—Ellen M. McAvoy
*Attorney, Agent, or Firm*—Madan & Morris, PLLC

[57] ABSTRACT

A water soluble corrosion inhibitor containing a compound having at least one five-membered heterocyclic ring having at least one thione group and at least one other pendant group is described. Such a corrosion inhibiting compound can be made by reacting together a thiourea and a polyalkylene polyamine. A specific example includes preparing 1-(2-aminoethyl)-2-imidazolidinethione by reacting thiourea, per se, and diethylenetriamine. These corrosion inhibition compounds have greatly reduced aquatic toxicity, and may be employed as corrosion inhibitors in hydrocarbon streams.

10 Claims, No Drawings

LOW TOXICITY CORROSION INHIBITOR

This application claims the benefit of U.S. Provisional Application No. 60/046,382 filed on May 13, 1997.

1. Field of the Invention

The present invention relates to corrosion inhibitors for hydrocarbons, and more particularly relates, in one embodiment to water soluble corrosion inhibitors having low aquatic toxicity.

2. Background of the Invention

It is well known that steel tubulars and equipment used in the production of oil and gas are exposed to corrosive environments. Such environments generally consist of acid gases ($CO_2$ and $H_2S$) and brines of various salinities. Under such conditions the steel will corrode, possibly leading to equipment failures, injuries, environmental damage and economic loss. Further in some cases, drilling fluids have acid intentionally added thereto in order to acidize the formations to enhance hydrocarbon recovering. This added acid also causes corrosion problems.

While the rate at which corrosion will occur depends on a number of factors such as metallurgy, chemical nature of the corrodent, salinity, pH, temperature, etc., some sort of corrosion almost inevitably occurs. One way to mitigate this problem consists of using corrosion inhibitors in the hydrocarbon production system.

It would be advantageous if a new corrosion inhibitor were discovered that would be an improvement over the presently known systems. In cases where the corrosion inhibitor may be present in the wastewater of a particular chemical, industrial, or hydrocarbon recovery process, it is further necessary and desirable to provide corrosion inhibitors which are of low toxicity in this era of greater environmental sensitivity.

SUMMARY OF THE INVENTION

Accordingly, it is an object of the present invention to provide a corrosion inhibitor that is effective in inhibiting the corrosion of steel surfaces in oil field tubing and equipment.

It is another object of the present invention to provide a corrosion inhibitor that has greatly reduced aquatic toxicity.

In carrying out these and other objects of the invention, there is provided, in one form, a water soluble corrosion inhibitor comprising a compound having at least one five-membered heterocyclic ring having at least one thione group and at least one other pendant group, the compound being present in an amount effective to reduce corrosion of a metal.

DETAILED DESCRIPTION OF THE INVENTION

It has been discovered that a water soluble corrosion inhibitor may be formed by the reaction of equimolar amounts of thiourea and diethylenetriamine to give 1-(2-aminoethyl)-2-imidazolidinethione. This reaction is schematically illustrated below:

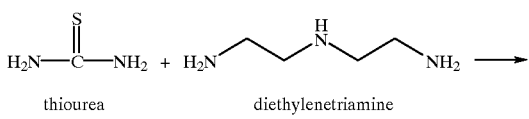

thiourea    diethylenetriamine

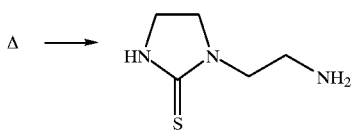

1-(2-aminoethyl)-2-imidazolidinethione

Ammonia, which is easily removed from the reactor, is a by-product of this process. The 1-(2-aminoethyl)-2-imidazolidinethione is produced with a yield of about 80%, based on the initial charge of the reactants.

The invention involves compounds of at least one five-membered heterocyclic ring having at least one thione group and at least one other pendant group which exhibit corrosion inhibiting properties. This is expected to be particularly true where the heterocyclic atoms in the five-membered ring include at least one nitrogen atom, and/or where the at least one other pendant group is terminated by an amine group or an hydroxyl group. In one embodiment of the invention, the compound preferably contains no hydroxyl groups.

U.S. Pat. No. 2,613,212 discloses 1-(2-aminoethyl)-2-imidazolidinethione, but only suggests it for the treatment of cellulosic materials or pesticides, not for corrosion inhibition.

The reactants used to make this invention include, but are not limited to sulfur-containing compounds such as thiourea, per se, and other thioureas, e.g. substituted thioureas, for example, alkyl, allyl, benzyl, phenyl, and vinyl thioureas, and mixtures thereof; and polyalkylene polyamines such as diethylenetriamine (DETA), triethylenetetramine, tetraethylenepentamine, and aminoethylethanolamine, and mixtures thereof. The thiourea and polyalkylene polyamine may be reacted at temperatures in the range from about 250° F. (121° C.) to about 500° F. (260° C.), preferably from about 300° F. (149° C.) to about 400° F. (204° C.). The reaction may be conducted at atmospheric pressures. A catalyst will not normally be required. The molar ratio of sulfur-containing compound to polyalkylene polyamine will vary depending upon the substituents desired in the final product. For example, if more thione groups are desired, the molar proportion of sulfur-containing compound required would be greater, whereas if more amine functionality is desired, a greater molar and/or equivalent proportion of polyalkylene polyamine would be necessary.

In the process of making the corrosion inhibitors of this invention, it is preferred to use nitrogen not only while cooling the product, but also during the reaction. This is crucial to the process. Further, it has been discovered that the reaction product can be used "as is" as a corrosion inhibitor without recrystallizing the final product. In one non-limiting embodiment of the invention, the molar ratio of thiourea to DETA may range from 1/1.25 to 1.25/1; preferably from 1/1.1 to 1.1/1, and is most preferably 1:1.

The water soluble, alicyclic (nonaromatic) heterocyclic thiones of this invention have greatly reduced aquatic toxicity. This characteristic is particularly important for offshore hydrocarbon recovery operations. Toxicological testing on 1-(2-aminoethyl)-2-imidazolidinethione gave a very high $EC_{50}$ (236 mg/l). Additionally, for Example 1 materials, $EC_{50}$=491 mg/l. Both results were obtained on *Skeletonema costatum*. The 1-(2-Aminoethyl)-2-imidazolidinethione prepared in Example 1 showed 100% biodegradability after 28 days (in sea water).

The 1-(2-aminoethyl)-2-imidazolidinethione compound of this invention is a light yellow, waxy solid in pure form. It would be commercialized in solution. Suitable solvent systems for 1-(2-aminoethyl)-2-imidazolidinethione would include, but are not limited to, water, in a non-limiting example, deionized (DI) water; alcohols, in a non-limiting example, methanol; glycols, in non-limiting examples butyl Carbitol™ and triethylene glycol (TEG); esters; ethers; and mixtures thereof. The solution can contain from about 10 to about 90% of the active compound, e.g. 1-(2-aminoethyl)-2-imidazolidinethione, with the balance being a solvent or a mixture thereof as described above.

The compounds of this invention should be present in a corrosion inhibitor in an amount effective to reduce corrosion of a metal contacting the fluid. The compounds of this invention will have utility in preventing and/or inhibiting corrosion of metals, particularly of steels, in hydrocarbon recovery environments, such as in the production of petroleum and/or natural gas from subterranean wells. They may be used in hydrocarbon streams, aqueous streams, and in combinations thereof such as emulsion streams including oil/water and water/oil emulsions. It will be appreciated that it is difficult to predict with accuracy what an effective amount will be for a particular application since there are a number of complex, interacting factors to be taken into account including, but not necessarily limited to, nature of the acidic medium, temperature of the medium, the nature of the metal being protected, and the like. It will be appreciated that one of ordinary skill in the art will be able to determine the proportion of corrosion inhibiting compound from merely routine trial and error. As a mere general and non-limiting indication, it is anticipated that a proportion range of the compounds of this invention in a hydrocarbon stream may range from about 5 to about 250 ppm, preferably from about 25 to about 100 ppm.

The invention will be further described with respect to the following Examples which are not limiting and intended only to further illustrate the invention.

EXAMPLE 1

1-(2-Aminoethyl)-2-imidazolidinethione Preparation

Thiourea, 228.3 g (76.1 molecular weight, 3 moles), and diethylenetriamine (DETA) 309.6 g (103.2 molecular weight, 3 moles) were charged to a 1-liter glass kettle equipped with a condenser, a stirrer and a gas inlet tube. The overhead condenser was turned on and a slow nitrogen sparge was started. Using an electric heating mantle, the mixture was heated to 350° F. (177° C.) while stirring. The reaction temperature was kept at 350° F. (177° C.) for 5 hours. The product, a viscous, yellow liquid, was allowed to cool to form a waxy solid. The overall yield was 76%. The following solutions were made up:

TABLE I

Solution Compositions

|  | Ex.1 | Ex.2 | Ex.3 | Ex.4 | Ex.5 | Ex.6 |
|---|---|---|---|---|---|---|
| 1-(2-aminoethyl)-2-imidazolidin-ethione | 40.9 g | 7.5 g | 3 g | 15.0 g | 15.0 g | 15.0 g |
| DI Water | 61.35 g | — | 12 g | 15.0 g | 10.0 g | 10.0 g |
| Butyl Carbitol | 61.35 g | — | — | — | 5.0 g | — |
| TEG | — | 42.5 g | — | — | — | — |
| Methanol | — | — | — | — | — | 5.0 g |

The proportions of 1-(2-Aminoethyl)-2-imidazolidinethione compound in these corrosion inhibiting solutions ranges from 15 wt. % (Example 2) to 50 wt. % (Examples 4–6). In one embodiment of the invention, the proportions of effective compound in these corrosion inhibitors ranges from about 5 wt. % to about 75 wt. %, preferably from about 20 wt. % to about 50 wt. %, and most preferably from about 15 wt. % to about 25 wt. %

Corrosion Test Results

Rotating Cylinder Electrode Test—Examples 7–20

A cylindrical steel coupon is rotated at 6000 rpm while immersed in a synthetic brine or a mixture of synthetic brine and kerosene. The fluids temperature is maintained at 150° F. (66° C.) and $CO_2$ is bubbled through the fluids for the duration of the test. The corrosion rate is measured by Linear Polarization Resistance and weight loss.

TABLE II

Rotating Cylinder Electrode Test Results

| Ex. | Inhibitor | Concentration (ppm) | Steady State Corrosion Rate (mpy) | % Inhibition | Weight Loss (mg) |
|---|---|---|---|---|---|
| Brine Kerosene | 90% 10% | 0 | 340 | — | 21 |
| 7 | Example 1 | 5 | 2.6 | 99.2 | 1.9 |
| 8 | Example 1 | 10 | 2.4 | 99.3 | 1.7 |
| 9 | Example 1 | 25 | 1.7 | 99.5 | 1.7 |
| 10 | Example 1 | 50 | 1.4 | 99.6 | 1.4 |
| 1% TEG | NaCl Brine 90% 60% | 0 | 80 | — | 13.0 |
| 11 | Example 2 | 8.3 | 70 | 12.5 | 9.4 |
| 12 | Example 2 | 16.7 | 30 | 62.5 | 4.5 |
| 13 | Example 2 | 33.3 | 15 | 81.3 | 3.8 |
| 14 | Example 2 | 83.3 | 9 | 88.8 | 5.5 |
| 15 | Example 2 | 166.7 | 10 | 87.5 | 2.4 |
| 16 | Example 2 | 166.7 | 8 | 90.0 | 5.4 |
| 17 | Example 2 | 333.3 | 3 | 96.3 | 2.8 |
| Brine Methanol | 95% 5% | 0 | 500 | — | 44.7 |
| 18 | Example 4 | 5 | 20 | 96.0 | 5.4 |
| 19 | Example 5 | 5 | 24 | 95.2 | 5.7 |
| 20 | Example 6 | 5 | 20 | 96.0 | 5.4 |

Bubble Test—Example 21

Cylindrical steel electrodes are immersed in a mixture of 80% synthetic brine and 20% kerosene. The fluids temperature is maintained at 50° C. and $CO_2$ is bubbled through the fluids for the duration of the test. The inhibitor is added on top of the organic phase. The corrosion rate is measured by Linear Polarization Resistance.

TABLE III

Bubble Test Results-Example 21

| | Corrosion Rate (mpy) | | | | |
|---|---|---|---|---|---|
| | Blank | 1 hr. | 2 hr. | 3 hr. | 4 hr. | 5 hr. |
| Example 3 (10 ppm) | 34.9 | 1.3 | 1.1 | 0.8 | 0.7 | 0.6 |

Wheel Test—Examples 22–25

A flat steel coupon is immersed in a mixture of 80% synthetic brine and 20% kerosene inside of a capped soda bottle. The gas space on top of the bottle is $CO_2$. The bottle is rotated for 24 hours while the temperature is maintained at 180° F. (82° C.) throughout the test. The corrosion rate is measured by weight loss.

TABLE IV

Wheel Test Results

| Ex. | Inhibitor | Concentration (ppm) | Weight Loss (mg) | % Inhibition |
|---|---|---|---|---|
| 22 | Blank | 0 | 0.0655 | — |
| 23 | Example 3 | 5 | 0.0091 | 86.1 |
| 24 | Example 3 | 10 | 0.0091 | 89.4 |
| 25 | Example 3 | 25 | 0.0058 | 91.2 |

In the foregoing specification, the invention has been described with reference to specific embodiments thereof, and has been demonstrated as effective in inhibiting corrosion. However, it will be evident that various modifications and changes can be made thereto without departing from the broader spirit or scope of the invention as set forth in the appended claims. Accordingly, the specification is to be regarded in an illustrative rather than a restrictive sense. For example, specific alicyclic, heterocyclic water soluble thione corrosion inhibitors made with sulfur-containing compounds and amines and/or alcohols falling within the claimed parameters, but not specifically identified or tried as reactants to make corrosion inhibitors herein, are anticipated to be within the scope of this invention.

I claim:

1. A water soluble corrosion inhibitor solution comprising a solvent; and
    a compound having at least one five-membered heterocyclic ring having at least one thione group and at least one other pendant group, where the other pendant group is selected from the group consisting of:
    —$CH_2CH_2NH_2$;
    —$CH_2CH_2NHCH_2CH_2NH_2$;
    —$CH_2CH_2NHCH_2CH_2NHCH_2CH_2NH_2$;
    —$CH_2CH_2OH$;
    and mixtures thereof;
    said compound being present in the solution in an amount effective to reduce corrosion of a metal.

2. The water soluble corrosion inhibitor solution of claim 1 where the compound is 1-(2-aminoethyl)-2-imidazolidinethione having the formula:

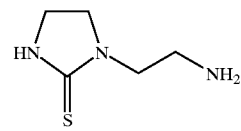

3. A method of inhibiting corrosion of metal in contact with a fluid comprising adding to the fluid an effective amount of a compound having at least one five-membered heterocyclic ring having at least one thione group and at least one other pendant group selected from the group consisting of:
    —$CH_2CH_2NH_2$;
    —$CH_2CH_2NHCH_2CH_2NH_2$;
    —$CH_2CH_2NHCH_2CH_2NHCH_2CH_2NH_2$;
    —$CH_2CH_2OH$;
    and mixtures thereof.

4. The method of inhibiting corrosion in a fluid of claim 3 where the compound is 1-(2-aminoethyl)-2-imidazolidinethione.

5. The method of inhibiting corrosion in a fluid of claim 3, where the fluid is involved in the production of a hydrocarbon from a subterranean well.

6. A method of preparing of a compound having at least one five-membered heterocyclic ring having at least one thione group and at least one other pendant group, comprising reacting a thiourea and a polyalkylene polyamine in the presence of nitrogen.

7. The method of claim 6 where the reaction is conducted at a temperature in the range of about 250° F. (121° C.) to about 500° F. (260° C.).

8. The method of claim 6 where the thiourea is thiourea and the polyalkylene polyamine is diethylenetriamine, and the compound prepared is 1-(2-aminoethyl)-2-imidazolidinethione.

9. The method of claim 8 where the molar ratio of thiourea to diethylenetriamine ranges from about 1/1.25 to 1.25/1.

10. The method of claim 8 where the amounts of thiourea and diethylenetriamine are equimolar.

* * * * *